(12) United States Patent
Hernandez

(10) Patent No.: US 12,201,549 B2
(45) Date of Patent: Jan. 21, 2025

(54) APPARATUS FOR REDUCING SNORING

(71) Applicant: David Hernandez, Bronx, NY (US)

(72) Inventor: David Hernandez, Bronx, NY (US)

( * ) Notice: Subject to any disclaimer, the term of this patent is extended or adjusted under 35 U.S.C. 154(b) by 0 days.

(21) Appl. No.: 16/520,584

(22) Filed: Jul. 24, 2019

(65) Prior Publication Data
US 2020/0030136 A1    Jan. 30, 2020

Related U.S. Application Data

(60) Provisional application No. 62/702,628, filed on Jul. 24, 2018.

(51) Int. Cl.
     *A61F 5/56*      (2006.01)

(52) U.S. Cl.
     CPC .................. *A61F 5/566* (2013.01)

(58) Field of Classification Search
     CPC ........... A61C 7/08; A61C 7/36; A61C 9/0006; A61F 5/56; A61F 5/566; A61F 2005/563; A63B 71/085; Y10S 602/902
     USPC .................... 128/848, 861; 433/46
See application file for complete search history.

(56) References Cited

U.S. PATENT DOCUMENTS

| | | | | | |
|---|---|---|---|---|---|
| 4,173,219 | A * | 11/1979 | Lentine | ............... | A61C 19/063 604/77 |
| 5,415,544 | A * | 5/1995 | Oxman | ............... | C08L 67/04 433/48 |
| 6,055,986 | A * | 5/2000 | Meade | ............... | A61F 5/566 128/859 |
| 6,886,566 | B2 * | 5/2005 | Eubank | ............... | A61C 7/08 128/859 |
| 8,534,289 | B2 * | 9/2013 | Hernandez | ............... | A61F 5/566 128/848 |
| 2011/0226261 | A1 * | 9/2011 | Hernandez | ............... | A61F 5/566 128/848 |
| 2013/0098372 | A1 * | 4/2013 | Webster | ............... | A61F 5/566 128/848 |
| 2014/0000633 | A1 | 1/2014 | Hernandez | | |

(Continued)

FOREIGN PATENT DOCUMENTS

| EP | 3167852 A1 * | 5/2017 | ............ A61F 5/566 |
|---|---|---|---|
| WO | 98/49981 A1 | 11/1998 | |
| WO | 2015/143043 A1 | 9/2015 | |

OTHER PUBLICATIONS

Extended European Search Report in corresponding EP application No. 19842157.0 dated Mar. 25, 2022.

(Continued)

*Primary Examiner* — Ophelia A Hawthorne
*Assistant Examiner* — Michael Milo
(74) *Attorney, Agent, or Firm* — Withers Bergman LLP; John C. Serio

(57) ABSTRACT

A mouthpiece has an upper guard having a first mold layer and a first shell layer. The upper guard has an arcuate shape between a first end on a first side and a second end on a second side. The mouthpiece also has a lower guard having a second mold layer and a second shell layer. The lower guard has arcuate shape between a third end on a third side and a fourth end on a fourth side. Connectors couple the ends of the upper guard to the ends of the lower guard. The first and second mold layer are a flexible material and the first and second shell layer are a relatively rigid material.

11 Claims, 5 Drawing Sheets

(56) References Cited

U.S. PATENT DOCUMENTS

| | | | |
|---|---|---|---|
| 2015/0223969 A1* | 8/2015 | Smith | A61F 5/56 128/861 |
| 2018/0193182 A1* | 7/2018 | Wiffen | A61F 5/58 |
| 2018/0207021 A1* | 7/2018 | Newby | A61F 5/566 |

OTHER PUBLICATIONS

International Search Report and Written Opinion for International Application No. PCT/US19/43144 dated Oct. 24, 2019.

* cited by examiner

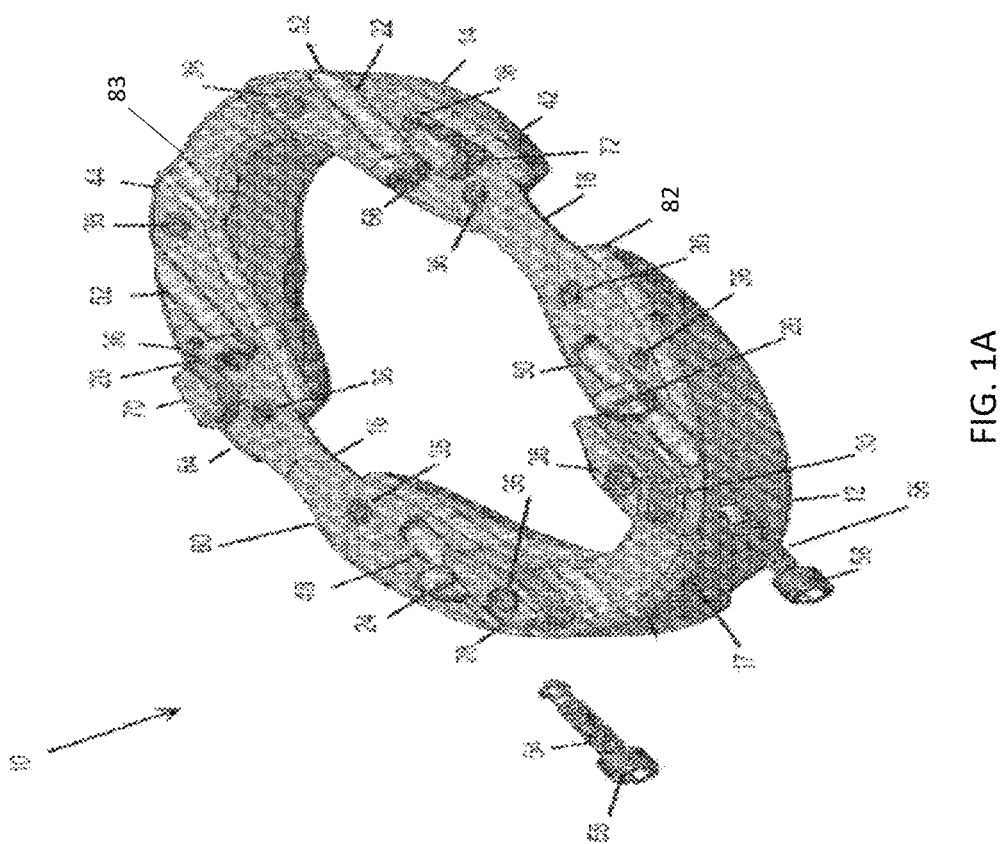

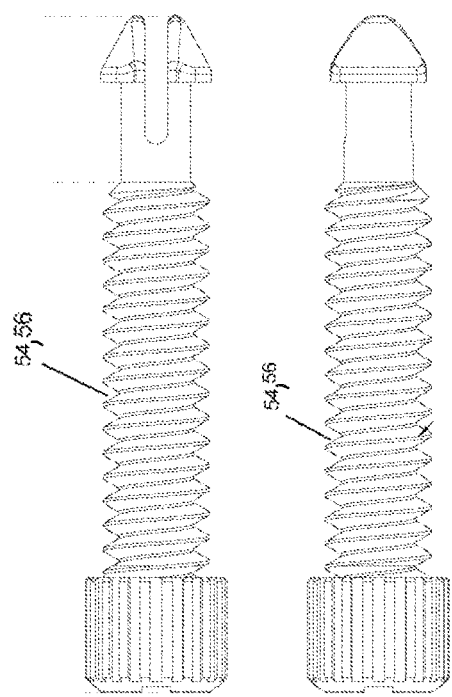
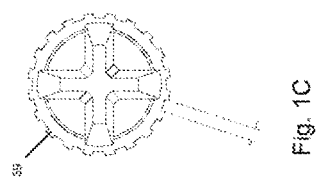
FIG. 1B
Fig. 1C

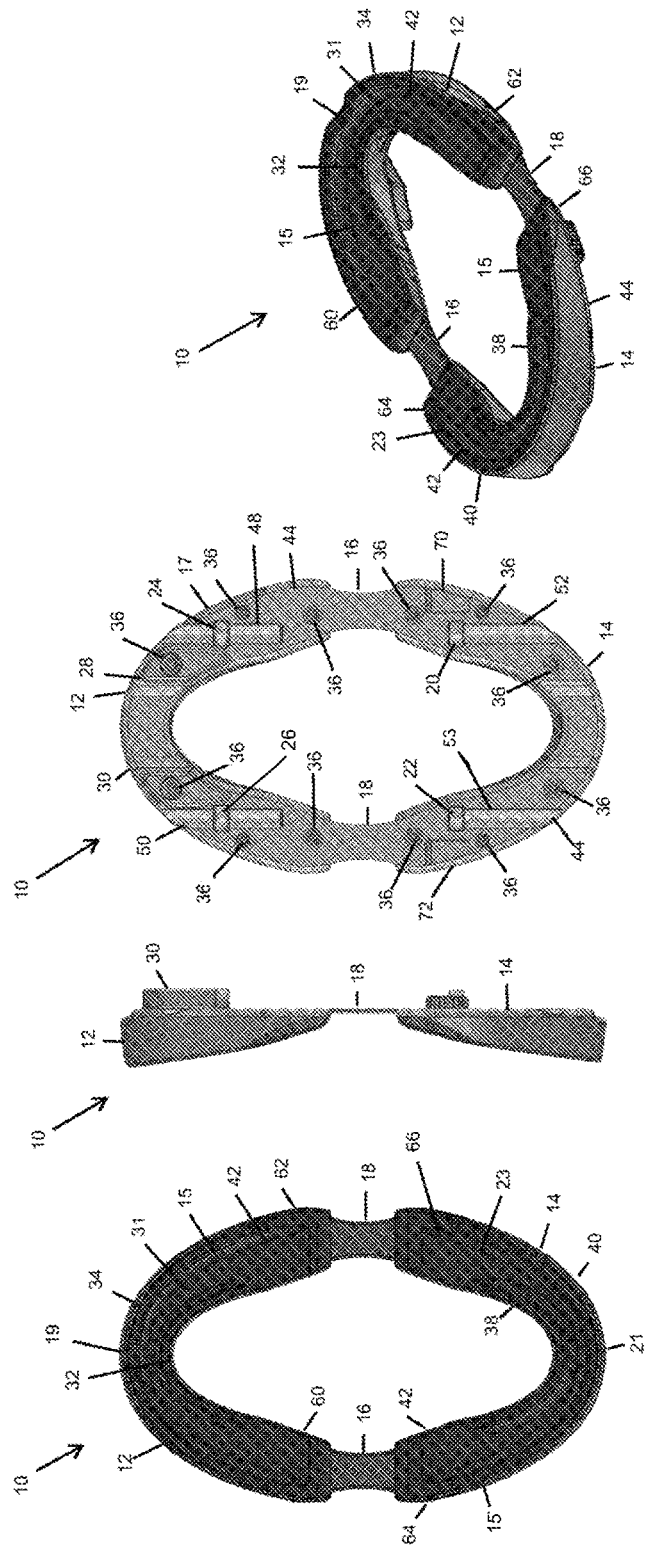

APPARATUS FOR REDUCING SNORING

RELATED APPLICATION

This application is a non-provisional application claiming priority to U.S. Provisional Application Ser. No. 62/702,628, filed on Jul. 24, 2018 entitled "SLEEP APNEA DEVICE," the entire contents of which is hereby incorporated by reference for all purposes.

FIELD

The subject technology relates to a device for reducing snoring. More particularly, the subject technology relates to adjustable mouthpieces for reducing snoring.

BACKGROUND

Snoring usually occurs when the airway of a sleeping person is restricted. Snoring can irritate those around the snorer. In some situations, the snorer may wish to reduce the snoring.

In some cases, a mouthpiece can be worn by the user when sleeping to reduce snoring. For example, U.S. Pat. No. 8,534,289 (the '289 patent) discloses a mouthpiece includes with an upper guard for the upper teeth and a lower guard for the lower teeth of a user. The upper and lower guards include notches to allow the mouthpiece to expand or contract to fit the widths of the user's jaws. The mouthpiece also includes an adjustable assembly on each of two sides of the mouthpiece, to allow the user to adjust the position of the lower guard relative to the upper guard. Using the adjustable assemblies, the user may adjustably bring the lower guard out toward the front of the mouthpiece, relative to the upper guard. With the lower guard being brought outward relative to the upper guard, the lower jaw of the user is brought out toward the front of the mouth. Because the lower jaw is brought outward, the normally restricted airway of the user opens during sleep. With the airway opens up, any resonance in the airway that causes snoring is reduced.

However, the mouthpiece disclosed in the '289 patent, and other available mouthpieces suffer from a number of deficiencies. For example, a flexible material is often used which can be molded by the teeth of a user. However, this material is also easily deformed and has trouble maintaining its form. This additionally limits the amount that the mouthpiece can be heated, which limits the extent that it can be molded around a user's teeth. Further, the pliable structure of such devices often means that external components, such as separators, must be employed to help the device keep a desired form. These problems can result in a mouthpiece which fits poorly in the mouth of a user.

SUMMARY

In light of the needs described above, in at least one aspect, there is a need for a mouthpiece which can maintain a rigid form while also allowing for the formation of deep impressions around the teeth of a user. Further, there is a need for a mouthpiece which fits comfortably in the mouth of the user and allows the user to breathe freely while also reducing snoring.

BRIEF DESCRIPTION OF THE DRAWINGS

So that those having ordinary skill in the art to which the disclosed system pertains will more readily understand how to make and use the same, reference may be had to the following drawings.

FIG. 1A is a bottom perspective view of a mouthpiece in accordance with the subject technology in an open position;

FIGS. 1B and 1C are a perspective view of the screw in accordance with the subject technology;

FIG. 2 is a top perspective view of a mouthpiece in accordance with the subject technology in an open position;

FIG. 3 is a top view of a mouthpiece in accordance with the subject technology in an open position;

FIG. 4 is a bottom view of a mouthpiece in accordance with the subject technology in an open position;

FIG. 5 is a side view of a mouthpiece in accordance with the subject technology in an open position;

DETAILED DESCRIPTION

Figure 6:
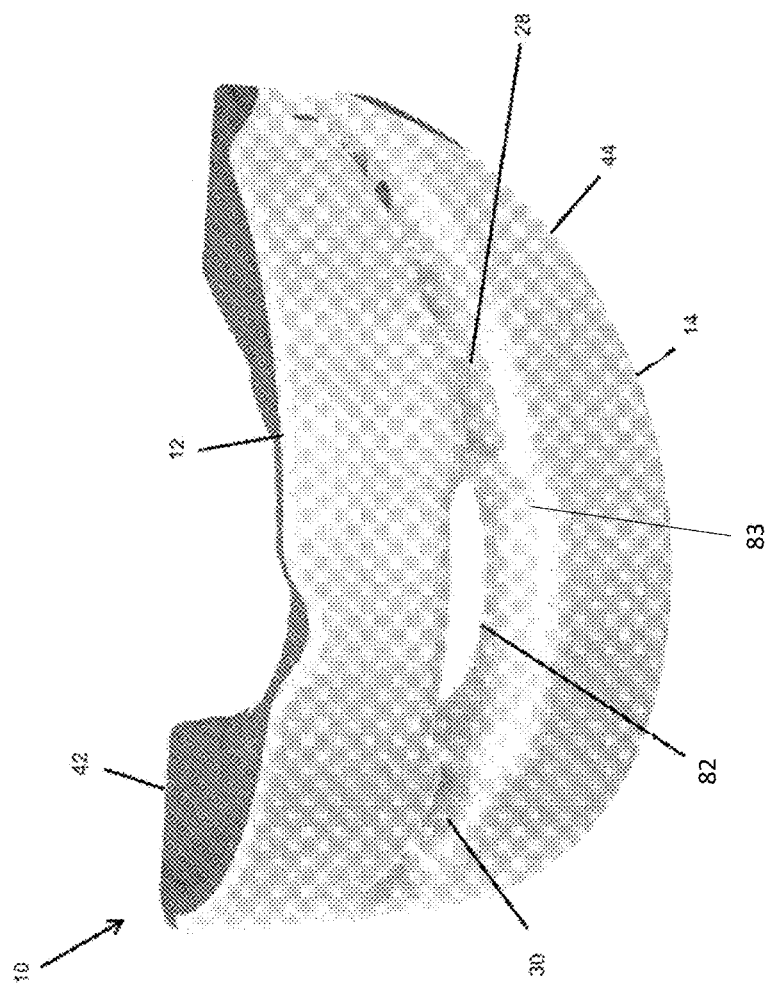
FIG. 6 is a front perspective view of a mouthpiece in accordance with the subject technology in a closed position.

Embodiments of the subject technology will now be described with reference to the drawing figures. To facilitate the description, a numeral designating an element in one figure will represent the same element in any other figure. The subject technology relates to a mouthpiece device for a user to use during sleep to reduce snoring.

Referring now to FIGS. 1-5, views of a mouthpiece 10 in accordance with the subject technology are shown. In all of FIGS. 1-5, the mouthpiece 10 is in an open and flat position prior to being closed for use. FIG. 1 is a bottom perspective view of the mouthpiece 10 while FIG. 2 is a top perspective of the mouthpiece 10. FIGS. 3 and 4 are top and bottom views of the mouthpiece, respectively. FIG. 5 is a side view of the mouthpiece.

As shown in FIGS. 1-5, the mouthpiece 10 generally includes an upper guard 12, a lower guard 14, a first adjustable assembly formed by guides 20, 24 and screw 54, a second adjustable assembly formed by guides 22, 26 and screw 56, and spacers 28, 30, 70, 72. The upper guard 12 is configured to fit over the upper teeth or gum of a user while the lower guard 14 is configured to fit over the lower teeth or gum of the user. The upper guard 12 and lower guard 14 are connected via two flexible connectors 16 and 18. When the mouthpiece 10 is in the open and flat position, as shown in FIGS. 1-5, the upper guard 12, the lower guard 14, and the connectors 16, 18 are coplanar for ease and economy of manufacture.

Details of the features of the mouthpiece 10 will now be described. The upper guard 12 is substantially an arch shape with a first end 60 connected to connector 16 and a second end 62 connected to connector 18. A bottom surface 17 of the upper guard 12, as shown in FIGS. 1 and 4, is substantially flat. The top surface 15 of the upper guard 12, as shown in FIGS. 2-3, defines a trough 31 to fit over the upper teeth or gum of the user. The trough 31 has an inner wall 32 and an outer wall 34. The height of the inner wall 32 is substantially even. In contrast, the height of the outer wall 34 gradually slopes up from the first and second ends 60, 62 attached to the connectors 16, 18, toward the center 19 of the arch formed by the upper guard 12.

Like the upper guard 12, the lower guard 14 is substantially an arch shape with a first end 64 connected to connector 16 and a second end 66 connected to connector 18. A bottom surface 17 of the lower guard 14, as shown in FIGS. 1 and 4, is substantially flat. The top surface 15 of the lower guard 14, as shown in FIGS. 2-3, defines a trough 23 to fit over the lower teeth or gum of the user. The trough 23 has an inner wall 38 and an outer wall 40. The height of the inner wall 38 is substantially even. In contrast, the height of the outer wall 40 gradually slopes up from the first and second ends 64, 66 attached to the connectors 16, 18, toward the center 21 of the arch formed by the lower guard 14.

The first adjustable assembly includes guides 20 and 24 and the first screw 54. The first screw 54 has a cylindrical head 58 and a threaded shank. The cylindrical head 58 of the first screw 54 has a hexagonal socket 59 to be driven by a hexagonal key 57. Similar to the first adjustable assembly, the second adjustable assembly includes guides 22 and 26 and the second screw 56. The second screw 56 has a cylindrical head 58 and a threaded shank. The cylindrical head 58 of the second screw 56 has a hexagonal socket 59 to be driven by a hexagonal key 57. Alternatively, other types of screws or heads may be used for the first and second screws 54, 56.

Still referring to FIGS. 1-5, the mouthpiece 10 is constructed from two separate layers; a mold layer 42 made and a shell layer 44. The upper guard 12 and lower guard 14, each include a portion of the overall mold layer 42 and shell layer 44. The mold layer 42 is positioned within the troughs 23, 31 so that when the mouthpiece 10 is in use, the mold layer 42 aligns with the teeth or gums of the user. The mold layer 42 is made from a flexible material that can be molded to form teeth impressions by the user after being heated in boiling water. In one illustrative embodiment the mold layer 42 can be a flexible thermoplastic such as ethylene-vinyl acetate (EVA). All other components of the mouthpiece 10 can be formed by the shell layer 44. In contrast to the mold layer 42, the shell layer 44 is a relatively rigid material which maintains a structural shape and will not deform or melt when heated or submerged in hot water. In one illustrative embodiment the shell layer 44 can be fabricated with injection molded polypropylene (PP). It is contemplated within the scope of the invention that other polymers may be used.

The shell layer 44 also includes a number of perforations through which anchors 36 from the mold layer 42 extend. When the mouthpiece 10 is heated, as will be described in more detail, the mold layer 42 and shell layer 44 are affected differently by thermal expansion. Therefore to help ensure that the mold layer 42 and shell layer 44 don't become separated during heating, the mold layer 42 includes anchors 36. The anchors 36 extend through perforations through the shell layer 44. The ends of the anchors 36 are wider than the perforations through the shell layer 44, such that the anchors 36 resist movement of the mold layer 42 away from the shell layer 44. Therefore the anchors 36 help ensure that the layers 42, 44 stay connected even when the mouthpiece 10 is heated.

Referring now to FIGS. 1-6, when assembled as shown in FIG. 6, the flexible connectors 16, 18 are bent such that the upper guard 12 is folded over the lower guard 14. Once assembled, the spacers 28, 30 on the lower guard 14 contact the upper guard 12 to maintain a separation distance and form central air passage 82 between the spacers 28, 30, upper guard 12, and lower guard 14. When the mouthpiece 10 is in the mouth of a user, the air passage 82 comprises a recess 83 and allows air to easily pass through the mouthpiece 10 so the user can breathe. Notably, the spacers 28, 30 can alternatively be fixed to the upper guard 12 such that they contact the lower guard 14. The mouthpiece 10 also, optionally, includes spacers 70, 72. Spacers 70, 72, are fixed, respectively, adjacent to the first and second ends 64, 66 of the lower guard 14. Spacers 70, 72 likewise extend from the lower guard 14 to maintain a gap between the upper guard 12 and the lower guard 14 when the mouthpiece 10 is in a closed position.

Further, when assembled as shown in FIG. 6, channels 48, 50, 52, 53 provide space in the upper and lower guards 12, 14 for the guides 20, 22, 24, 26, and screws 54, 56. In particular, the first adjustable assembly is formed when guide 20 aligns with guide 24 within channels 48, 52. Screw 54 can then be passed through the guides 20, 24. Exterior threads of the screw 54 couple with interior threads of the guide 20. The head 58 of the screw 54 is wide enough that it won't pass through the guide 24. Therefore when the screw 54 is tightened, the exterior threads pull the screw 54 deeper into the guide 20, and the head 58 of the screw 54 pulls the guide 24 closer to the guide 20. Similarly, the second adjustable assembly is formed when guide 22 aligns with guide 26 within channels 50, 53. Screw 56 can then be passed through the guides 22, 26. Exterior threads of the screw 54 couple with interior threads of guide 22. The head 58 of the screw 56 is wide enough that it won't pass through the guide 26. Therefore when screw 56 is tightened, the exterior threads pull the screw 56 deeper into the guide 22, and the head 58 of the screw 56 pulls the guide 26 closer to the guide 22. As is discussed in more detail below, the first and a second adjustable assembly can be adjusted in this way to modify the mouthpiece 10 and attain a desired fit for a user.

Before using the mouthpiece 10, a user can mold the mouthpiece 10 and adjust it to a proper fit. To start, the user can submerge the entire fully assembled mouthpiece 10 (as seen in FIG. 6) in boiling water, leaving the mouthpiece 10 submerged for about 90 seconds so that the mold layer 42 can fully heat up and reach an ideal level of pliability. During this time, although the mold layer 42 becomes much easier to deform, the shell layer 44 retains its shape, and therefore, retains the overall shape and structure of the mouthpiece 10. The user can then briefly submerge the mouthpiece 10 in cold water (e.g. for about three seconds) to rinse off the boiling water and cool the exterior of the mouthpiece 10 down slightly. Then, the user can insert the mouthpiece 10 into their mouth with the trough 31 fitting over the upper teeth or gum and the trough 23 fitting over the lower teeth or gum. The user then bites down to form teeth impressions within the mold layer 42. In some cases, biting down firmly for about 30 seconds can form deep impressions in the mold layer 42. Throughout this process the shell layer 44 prevents deformation of the mouthpiece 10 itself or components thereof. After the impressions have been formed in the mold layer 42, the user can submerge the mouthpiece 10 in cold water for around 30 seconds to cool and re-harden the mold layer 42. If deep impressions did not form in the mold layer 42, the process of heating the mouthpiece 10 and forming the impressions can be repeated as needed.

Referring now to FIGS. 7-10, after the impressions are formed, further adjustments can be made to the mouthpiece 10. The first and second adjustable assemblies allow the respective positions of the upper guard 12 and lower guard 14 to be changed depending on the preference of the user.

Specifically, the screws 54,56 can be manipulated with a hexagonal key 57 to extend the lower guard 14 outward with respect to the mouthpiece 10. By adjusting the respective positions of the upper guard 12 and the lower guard 14 to an ideal position for a given user, snoring can be reduced.

Figure 7:
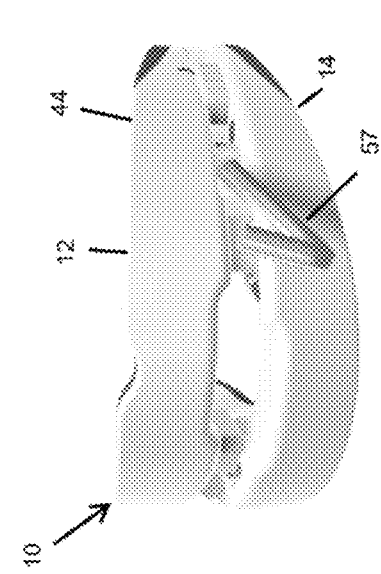
FIG. 7 is a front perspective view of a closed mouthpiece in accordance with the subject technology just prior to being adjusted.
Figure 8:
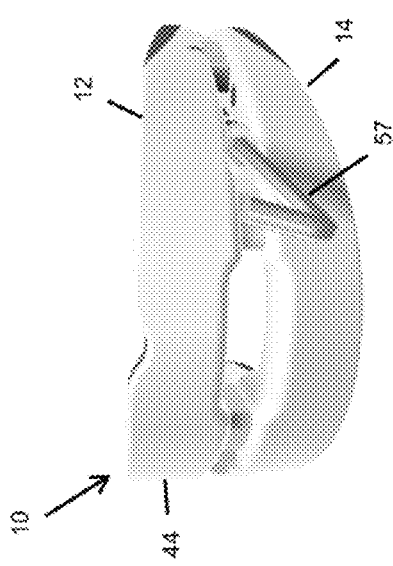
FIG. 8 is a front perspective view of a closed mouthpiece in accordance with the subject technology in the process of being adjusted.

To that end, FIG. 7 shows the mouthpiece 10 prior to any adjustments. In this position, the upper guard 12 is positioned directly above the lower guard 12. When the user desires to make an adjustment to the first adjustable assembly, the hexagonal key 57 can be inserted into the hexagonal socket 59 in the head 58 of screw 54. As the hexagonal key is 57 is turned, the screw 54 turns and the threaded exterior of the screw 54 travels deeper into the threaded guide 20. Since the head 58 of the screw 54 is against the guide 24, turning the screw 54 pulls the guide 24 closer to the guide 20. This causes the lower guard 14 to extend forward (i.e. in a direction out of a user's mouth when in use) with respect to the upper guard 12. As can be seen in FIG. 8, when only one adjustable assembly is adjusted in this way, only the corresponding half of the lower guard 14 will extend forward from the upper guard 12.

Figure 9:
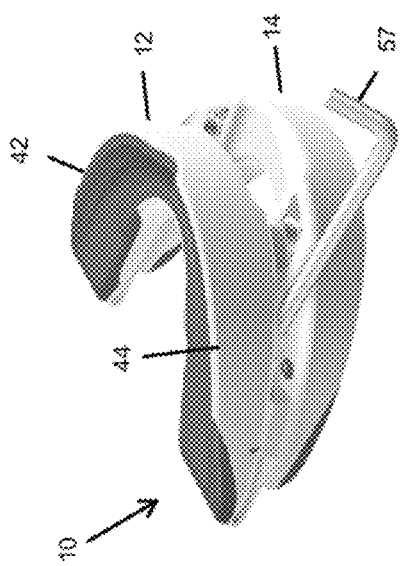
FIG. 9 is a front perspective view of a closed mouthpiece in accordance with the subject technology in the process of being adjusted.
Figure 10:
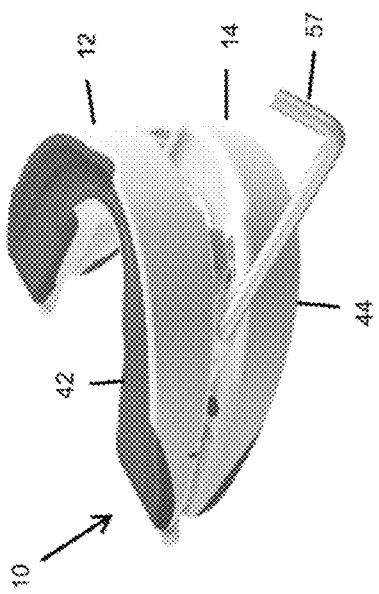
FIG. 10 is a front perspective view of a closed mouthpiece in accordance with the subject technology subsequent to being adjusted.

Turning to FIG. 9, a corresponding adjustment can then be made to the second adjustable assembly. To that end, the hexagonal key 57 can be inserted into the hexagonal socket 59 of the screw 56 on the other side of the mouthpiece 10. As the hexagonal key 57 is turned, the screw 56 turns and the threaded exterior of the screw 56 travels deeper in the threaded guide 22. Since the head 58 of the screw 56 is against the guide 26, turning the screw 56 pulls the guide 26 closer to the guide 22. This causes the lower guard 14 to extend forward with respect to the upper guard 12. When both the first and second assemblies have been adjusted equally, as can be seen in FIG. 10, the entire lower guard 14 will be a uniform distance forward of the upper guard 12.

In this way, the mouthpiece 10 can be adjusted such that when a user places the mouthpiece 10 in their mouth, the mouthpiece 10 urges the lower jaw of the user into a forward position. Urging the lower jaw forward opens up the airway of the user, allowing air to flow freely through the back of the user's throat. This greatly reduces snoring which is caused by a partially obstructed airway leading to turbulent airflow and vibration in the nose and throat. Further, the mouthpiece 10 provides a cushion between the teeth of the user which can prevent the user from grinding their teeth while they sleep.

It is to be understood that the above detailed description of the embodiments of the subject technology is provided by way of example only. Various details of design, construction and procedure may be modified without departing from the spirit and scope of the subject technology, as set forth in the appended claims.

The invention claimed is:

1. A mouthpiece for reducing snoring comprising: an upper guard configured to fit over the upper teeth or gum of a user, the upper guard comprising a first mold layer forming a top surface and a first shell layer forming a bottom surface, the upper guard having an arcuate shape between a first end on a first side of the upper guard and a second end on a second side of the upper guard; a lower guard configured to fit over the lower teeth or gum of the user, the lower guard comprising a second mold layer forming a top surface and a second shell layer forming a bottom surface, the lower guard having an arcuate shape between a third end on a third side of the lower guard and a fourth end on a fourth side of the lower guard, wherein the first and second mold layer are ethylene-vinyl acetate; a first connector coupling the first end of the upper guard and the third end of the lower guard; and a second connector coupling the second end of the upper guard and the fourth end of the lower guard; a first adjustable assembly comprising: a first channel defined in the bottom surface of the upper guard on the first side; a first guide positioned in, and fixed to, the first channel; a second channel defined in the bottom surface of the lower guard on the third side; a second guide positioned in, and fixed to, the second channel; and a first screw configured to engage the first guide and the second guide to adjust the respective positions of the upper guard and the lower guard when the mouthpiece is in a closed position, wherein the first screw comprises a respective first head that is accessible from a front of the mouthpiece; and a second adjustable assembly comprising: a third channel defined in the bottom surface of the upper guard on the second side; a third guide positioned in, and fixed to, the third channel; a fourth channel defined in the bottom surface of the lower guard on the fourth side; a fourth guide positioned in, and fixed to, the fourth channel; and a second screw configured to engage the third guide and the fourth guide to adjust the respective positions of the upper guard and the lower guard when the mouthpiece is in the closed position, wherein the second screw comprises a respective second head that is accessible from the front of the mouthpiece, wherein the first connector and the second connector are flexible to allow the upper guard to fold over the lower guard when the mouthpiece is in the closed position, wherein the first and second shell layer are a rigid or a semi-rigid material, wherein said first and second layers having a plurality of perforations extending through said first and second shell layers; and the first and second mold layers each include a plurality of anchors extending through the perforations to bind the mold layers of the upper and lower guards to the shell layers of the upper and lower guards, respectively; each of the first, second, third, and fourth guides consisting of a respective guiding portion having a same first semi-circular cross-sectional shape extending beyond, respectively, the bottom surface of the upper guard on the first side, the bottom surface of the lower guard on the third side, the bottom surface of the upper guard on the second side, and the bottom surface of the lower guard on the fourth side; each of the first, second, third, and fourth channels comprises a cross-sectional shape configured to receive the guiding portion of an opposing guide when the mouthpiece is in the closed position; wherein the mouthpiece further comprises a first spacer and a second spacer fixed to, and extending from, a front portion of the bottom surface of the upper guard to define a central air passage and a third spacer as well as a fourth spacer fixed to, and extending from, a rear portion of the top surface; wherein the first spacer, the second spacer, the third spacer, and the fourth spacer do not contact one another.

2. The mouthpiece of claim 1, wherein, when the mouthpiece is in the closed position:
   each of the first, second, third, and fourth channels receives and aligns the guiding portion of the opposing guide.

3. The mouthpiece of claim 2, wherein, when the mouthpiece is in the closed position:
   the first guide and the second guide are aligned with one another within the second and first channels, respectively; and
   the third guide and the fourth guide are aligned with one another within the fourth and third and fourth channels.

4. The mouthpiece of claim 3, wherein, when the mouthpiece is in the closed position:
   the first channel receives the second guide guiding portion;

the second channel receives the first guide guiding portion;

the third channel receives the fourth guide guiding portion; and the fourth channel receives the third guide guiding portion.

5. The mouthpiece of claim 1, wherein the first and second mold layers are configured to allow a user to form teeth impressions therein after the mouthpiece has been heated.

6. The mouthpiece of claim 5, wherein the first and second shell layer are configured to maintain a rigid structural shape when the mouthpiece is heated.

7. The mouthpiece of claim 1, wherein the first and second shell layers are polypropylene.

8. The mouthpiece of claim 1, wherein:

the top surface of the upper guard includes an inner wall and an outer wall defining a trough; and the top surface of the lower guard includes an inner wall and an outer wall defining a trough.

9. The mouthpiece of claim 1, wherein each of the first, second, third, and fourth channels comprises a concave semi-circular shape, corresponding to the first semi-circular cross-sectional shape, in its respective surface.

10. The mouthpiece of claim 1, wherein the mouthpiece is in the closed position when the upper and lower guards are positioned with respective bottom surfaces opposing one another.

11. The mouthpiece of claim 1, wherein the central air passage is unobstructed and an anterior front portion of the upper and lower guards comprise a recess to form a greater sized unobstructed central air passage.

\* \* \* \* \*